United States Patent

Kimura et al.

Patent Number: 5,946,543
Date of Patent: Aug. 31, 1999

[54] SEMICONDUCTOR WAFER EVALUATING METHOD AND SEMICONDUCTOR DEVICE MANUFACTURING METHOD

[75] Inventors: Yasuhiro Kimura; Morihiko Kume, both of Tokyo; Tsuneaki Fujise; Masanori Gohara, both of Saga, all of Japan

[73] Assignees: Mitsubishi Denki Kabushiki, Tokyo; Sumitomo Sitix Corporation, Hyogo, both of Japan

[21] Appl. No.: 09/008,656

[22] Filed: Jan. 16, 1998

[30] Foreign Application Priority Data

Jun. 2, 1997 [JP] Japan ................... P09-143910

[51] Int. Cl.$^6$ .................... H01L 21/66
[52] U.S. Cl. ............ 438/14; 438/17; 148/DIG. 162
[58] Field of Search ............... 438/14, 15, 16, 438/17; 148/DIG. 162

[56] References Cited

U.S. PATENT DOCUMENTS

| 5,233,191 | 8/1993 | Noguchi et al. | 438/16 |
| 5,389,551 | 2/1995 | Kamakura et al. | 438/423 |
| 5,464,779 | 11/1995 | Fujimaki | 438/16 |

FOREIGN PATENT DOCUMENTS 4-212433  8/1992  Japan.
7-206591  8/1995  Japan.

OTHER PUBLICATIONS

Keigo Hikawa, Baifukan, pp. 60–63, "Bulk Crystal Growth Technique" date unknown.

Realize Co., USC Semiconductor Substrate Technique Research Institute, pp. 300–301, "The Science of Silicon" date unknown.

*Primary Examiner*—Kevin M. Picardat
*Attorney, Agent, or Firm*—Oblon, Spivak McClelland, Maier & Neustadt, P.C.

[57] ABSTRACT

An object is to obtain a semiconductor wafer evaluation method and a semiconductor device manufacturing method having a reduced turn-around time and requiring no process apparatus and no dielectric breakdown characteristic evaluation device in evaluation of the dielectric breakdown characteristic of the oxide film. A sample wafer (1) is etched by using an SC-1 solution bath (2) to change process defects caused in the fabrication process including mirror polishing into pits. The number of pits is detected with a dust particle inspection system, and the dielectric breakdown characteristic of the sample wafer 1 can be evaluated by using the number of detected pits and previously obtained relations between the number of pits and the dielectric breakdown characteristic.

6 Claims, 11 Drawing Sheets

SEMICONDUCTOR WAFER EVALUATING METHOD AND SEMICONDUCTOR DEVICE MANUFACTURING METHOD

BACKGROUND OF THE INVENTION

1. Field of the Invention

The present invention relates to a semiconductor wafer evaluating method for obtaining semiconductor devices having reliable gate oxide film, a semiconductor device manufacturing method for manufacturing semiconductor devices by using semiconductor wafers evaluated by the evaluating method.

2. Description of the Background Art

With the miniaturization and the increase in formation area of the semiconductor integrated circuits, improvements in reliability of the gate oxide film in MOS devices are becoming increasingly important. The reliability of the gate oxide film depends on the quality of the semiconductor wafer on which the gate oxide film is formed. Accordingly, obtaining a semiconductor device having highly reliable gate oxide film requires prior evaluation of the semiconductor wafer in manufacturing.

The following have been considered to be the main factors which affect the reliability of the gate oxide film:

(1) Quality of silicon crystal based on oxygen concentration in the silicon crystal;

(2) Quality of silicon crystal based on crystal defects caused by heat history in the single-crystal growth; and (3) Quality of silicon crystal based on behavior of crystal defects caused by heat treatment before formation of the gate oxide film.

Recently, with the use of lower temperatures in the semiconductor manufacturing processes, the following is also considered as a factor which affects the reliability of the gate oxide film, as well as the factors (1) to (3) above:

(4) Quality of silicon crystal based on process defects caused in processes including the mirror polishing.

Evaluation of semiconductor wafers is described in Japanese Patent Laying-Open No.4-212433 and Japanese Patent Laying-Open No.7-206591, for example. These two references describe the crystal defects in the substrate surface as a cause, attributed to the semiconductor wafer, of the reduction in yield of devices formed on the semiconductor wafer, but neither of the two describes the factor (4) shown above.

For the purpose of obtaining a semiconductor device having highly reliable gate oxide film, a conventional evaluation of semiconductor wafers in manufacturing semiconductor devices is conducted by using actually formed gate oxide film. That is to say, a test pattern of the MOS structure having gate oxide film is actually formed on a mirror-polished object semiconductor wafer by applying processing such as oxidization, patterning, formation of interconnections, etc. with process apparatus. Next, the dielectric breakdown characteristic of the oxide film is measured with the test pattern by using a device (e.g., a tester) for measuring the dielectric breakdown characteristic (e.g., the TDDB (Time Dependent Dielectric Breakdown) characteristic). Next, the semiconductor wafer is evaluated from the measurements.

The above-described semiconductor wafer evaluation in fabrication of semiconductor devices, however, has the following problems:

(1) Forming the test pattern on a sample wafer requires a long turn-around time from the start of evaluation to the evaluation of the semiconductor wafers;

(2) It requires process equipment for forming the test pattern; and (3) It requires a device for evaluating the dielectric breakdown characteristic.

SUMMARY OF THE INVENTION

According to a first aspect of the present invention, a semiconductor wafer evaluation method comprises the steps of: (a) preparing a mirror-polished semiconductor wafer; (b) changing a process defect caused by grinding and polishing including the mirror polishing into a pit and also changing a defect under the surface of the semiconductor wafer into a pit having a detectable size; (c) detecting the number of pits on the semiconductor wafer surface after the step (b); and (d) evaluating the oxide film dielectric breakdown characteristic of the semiconductor wafer on the basis of the number of pits detected in the step (c).

Preferably, according to a second aspect, in the semiconductor evaluation method, the step (b) comprises the step of removing the semiconductor wafer to a position deeper than 20 nm in the semiconductor wafer from the surface of the semiconductor wafer.

Preferably, according to a third aspect, in the semiconductor wafer evaluation method, the step (b) comprises the step of removing the surface of the semiconductor wafer by using a mixed solution of $NH_4OH$, $H_2O_2$, and $H_2O$.

Preferably, according to a fourth aspect, in the semiconductor wafer evaluation method, the step (b) comprises the step of heating the semiconductor wafer to form an oxide film on the surface of the semiconductor wafer and then removing the oxide film by using a solution which can remove only the oxide film without dissolving the semiconductor wafer.

Preferably, according to a fifth aspect, in the semiconductor wafer evaluation method, the step (a) comprises the steps of (a-1) preparing a plurality of semiconductor wafers in a certain lot, and (a-2) extracting a certain number of semiconductor wafer(s) as sample wafer(s) from the plurality of semiconductor wafers in the lot, wherein the semiconductor wafer evaluation method further comprises the step of (e) judging the lot to be acceptable when the evaluation in the step (d) shows that the sample wafer is acceptable.

Preferably, according to a sixth aspect of the present invention, a semiconductor device manufacturing method comprising the steps of: (a-1) preparing a plurality of mirror-polished semiconductor wafers in a certain lot; (a-2) extracting predetermined number of semiconductor wafer(s) as sample wafer(s) from the plurality of semiconductor wafers in the lot; (b) changing a process defect caused by grinding and polishing including the mirror polishing into a pit and also changing a defect under the surface of the sample wafer(s) into a pit having a detectable size; (c) detecting the number of pits on the sample wafer(s) surface after the step (b); and (d) evaluating an oxide film dielectric breakdown characteristic of the sample wafer(s) on the basis of the number of pits detected in the step (c); and (e) judging the lot to be acceptable when the evaluation in the step (d) shows that the sample wafer is acceptable, wherein predetermined semiconductor devices are formed on the semiconductor wafers in the lot which is judged to be acceptable in the step (e).

According to the first aspect of the present invention, process defects caused by process of mirror polishing (grinding and polishing) and the like are changed into pits, and defects under the surface of the semiconductor wafer are also changed into pits having detectable sizes. Then the dielectric breakdown characteristic of oxide film of the semiconductor wafer can be evaluated on the basis of the number of pits. This enables the process defects to be taken into consideration, eliminates the necessity of forming the test pattern, leading to reduction in turn-around time, and eliminates the necessity for the process device and the dielectric breakdown characteristic evaluation device.

According to the second aspect, the number of pits detected in the step (c) with the semiconductor wafer removed to a position in the semiconductor wafer deeper than 20 nm from the surface of the semiconductor wafer is much larger than that with the semiconductor wafer removed only to a position in the semiconductor wafer shallower than 20 nm from the surface. That is to say, when the semiconductor wafer is removed to a position in the semiconductor wafer deeper than 20 nm from the surface, the process defects can be detected more correctly.

According to the third aspect, etching the semiconductor wafer by using a mixed solution of $NH_4OH$, $H_2O_2$ and $H_2O$ can change process defects caused by process including mirror polishing into pits, and can also change defects under the semiconductor wafer surface into pits having sizes detectable by a dust particle inspection system.

According to the fourth aspect, heating the semiconductor wafer to form an oxide film on the surface of the semiconductor wafer and then removing the oxide film with a solution which can remove only the oxide film without dissolving the semiconductor wafer provides the same effect as the third aspect, i.e., the effect of changing the process defects caused by the process of mirror polishing or the like into pits and also changing the defects under the surface of the semiconductor wafer into pits large enough to be detected by a dust particle inspection system.

According to the fifth aspect, when a sample wafer is evaluated to be an acceptable product, the lot is regarded as being acceptable, which provides the effect of eliminating the necessity of evaluating each semiconductor wafer.

According to the sixth aspect, forming predetermined semiconductor devices on the semiconductor wafers in the lot judged to be acceptable improves the yield of the semiconductor devices and suppresses variation in the yield.

The present invention has been made to solve the problems stated above, and it is an object of the present invention to obtain a semiconductor wafer evaluating method and a semiconductor device manufacturing method which reduce the turn-around time for evaluation, requires no process device and no oxide dielectric breakdown characteristic evaluating device, and which consider process defects caused by the manufacturing process such as mirror polishing.

These and other objects, features, aspects and advantages of the present invention will become more apparent from the following detailed description of the present invention when taken in conjunction with the accompanying drawings.

DESCRIPTION OF THE PREFERRED EMBODIMENTS

First Preferred Embodiment

Figure 1:
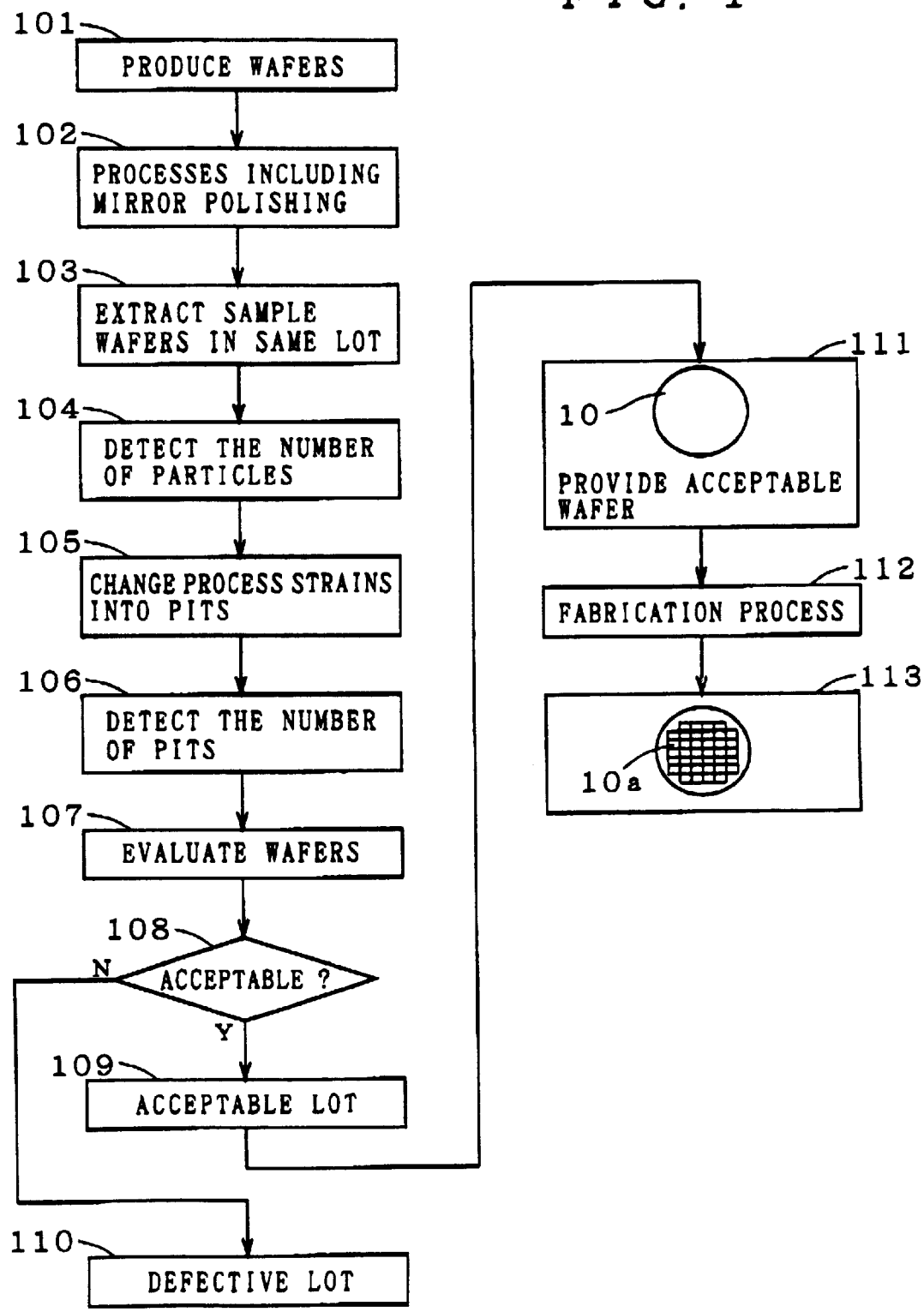
FIG. 1 is a flow chart showing a semiconductor wafer evaluation method and a semiconductor device manufacturing method of the invention.

First, a semiconductor device manufacturing method in a first preferred embodiment of the invention will be described referring to FIG. 1 to FIG. 4. FIG. 1 is a flow chart showing the semiconductor wafer evaluation method and the semiconductor device manufacturing method of the invention.

Referring to step 101, a plurality of semiconductor wafers are manufactured by cutting one grown semiconductor ingot.

Next, referring to step 102, the plurality of semiconductor wafers manufactured in step 101 are subjected to processings, such as mirror polishing (grinding and polishing). The plurality of semiconductor wafers processed in step 102 correspond to a plurality of semiconductor wafers in a lot. Thus, a plurality of semiconductor wafers in a certain lot are prepared in step 102. It is assumed that process defects are caused on the plurality of semiconductor wafers in this lot in the process of mirror polishing and the like.

Figure 2:
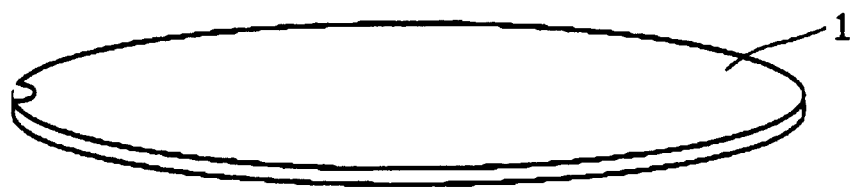
FIG. 2 is a drawing schematically showing a particle number detecting step in FIG. 1 in a first preferred embodiment of the present invention.

Next, referring to step 103, a certain number of semiconductor wafers are extracted as sample wafers from the plurality of semiconductor wafers in the lot prepared in step 102. The certain number may be single or may be plural. FIG. 2 shows an example of a sample wafer extracted in step 103. The size of the sample wafer 1 shown in FIG. 2 is 200 mmφ and it is mirror-polished.

In this way, mirror-polished semiconductor wafers are finally prepared in steps 101 to 103.

Next, referring to step 104, the number of particles on the surface of the sample wafer 1 shown in FIG. 2 is detected by using a dust particle inspection system. As for the dust particle inspection system, Surfscan6200 produced by Tencor is used, for example. This device detects particles having sizes of about 0.10 to 0.14 $\mu m\phi$ or larger.

Figure 5:
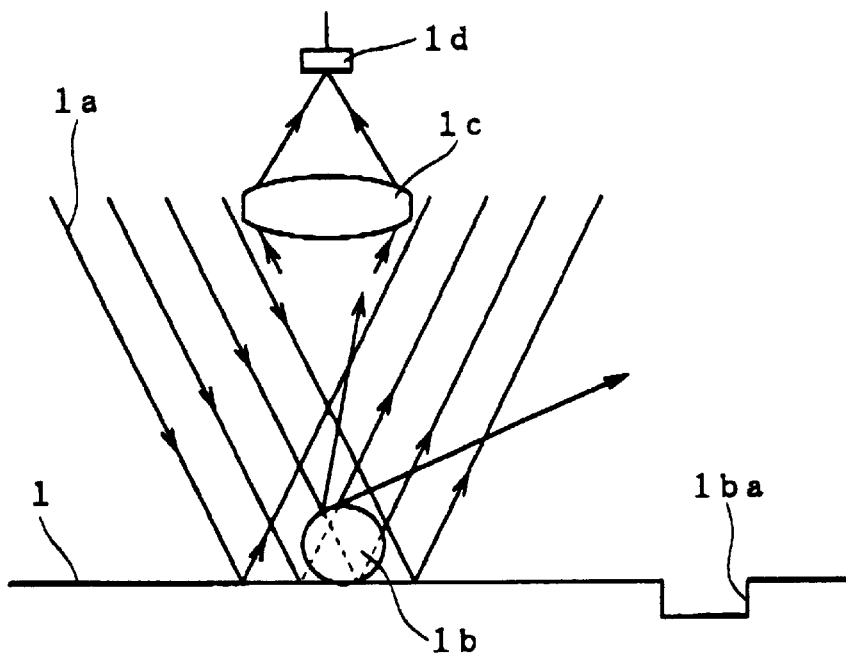
FIG. 5 is an explanation drawing showing the principle of detection of particles.

The particles are detected according to the following principle. That is to say, referring to FIG. 5, when the surface of the sample wafer 1 is scanned with laser light 1a, a dust particle 1b causes light scattering. The detector 1d (e.g., a photodiode) detects the light scattering through the lens 1c. The dust particle inspection system measures the intensity of the detected light scattering to detect the position and size of the dust particle 1b. Particles detected by the dust particle inspection system include, as well as the dust particle 1b attached on the surface of the sample wafer 1, a pit 1ba of a crystal defect (Crystal Originated Particle).

When the sample wafer 1 is manufactured on a processing line with cleanliness sufficiently controlled, the number of the particles of 0.12 $\mu m\phi$ or larger is usually 0–100. In this case, the particles mainly include pits 1ba, since the dust particles 1b attached on the surface of the sample wafer 1 are cleaned away.

If the number of particles detected in step 104 is larger than a predetermined number, it is possible to consider all of the plurality of semiconductor wafers in the lot of this sample wafer 1 to be defective products at this point of time.

Figure 3:
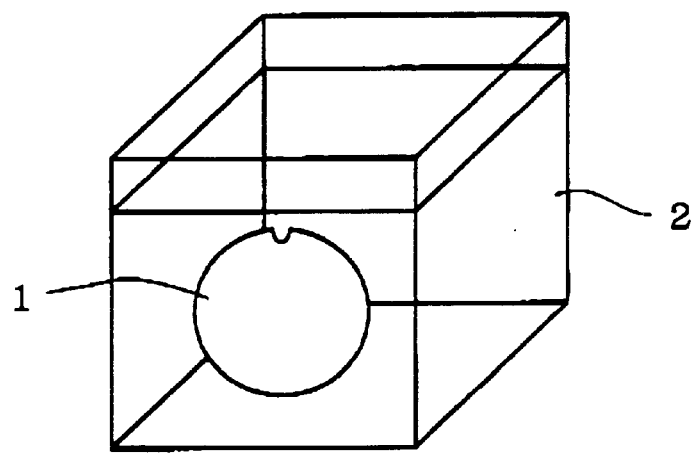
FIG. 3 is a drawing schematically showing a process strain changing step in FIG. 1 in a first preferred embodiment of the present invention.

Next, referring to step 105, the sample wafer 1 is immersed into an SC-1 solution bath 2 as shown in FIG. 3. This SC-1 solution bath 2 is filled with a mixed solution of $NH_4OH$, $H_2O_2$, and $H_2O$. When the sample wafer 1 is immersed in the SC-1 solution bath 2, formation of oxide film and removal of the oxide film are simultaneously achieved on the surface of the sample wafer 1. With the formation and removal of the oxide film, the surface of the sample wafer 1 is etched away. Particularly, since a large amount is etched at process defects, the process defects change into pits. Thus the etching causes the defects under the surface of the semiconductor wafer, or the pits originated from the process defects and the pits already existing in step 102, to change into pits large enough to be detected by the dust particle inspection system.

In step 105, the dust particles 1b (refer to FIG. 5) attached on the surface of the sample wafer 1 in FIG. 2 are removed simultaneously with the removal of the oxide film. Thus, in step 105, removing the surface of the sample wafer 1 by using SC-1 changes the process defects caused in the process such as mirror polishing into pits, and also changes the defects under the surface of the sample wafer 1 into pits so large as to be detected by the dust particle inspection system.

Figure 4:
FIG. 4 is a drawing schematically showing a pit number detecting step in FIG. 1 in a first preferred embodiment of the present invention.

Next, after step 105, referring to step 106, the sample wafer 1 is taken out from the SC-1 solution bath 2. The sample wafer 1 shown in FIG. 4 shows the sample wafer taken out from the SC-1 solution bath 2. Since the dust particles have been removed in step 105 as stated above, the particles on the surface of the sample wafer 1 taken out from the solution bath 2 mainly include pits. Then the pits on the surface of the sample wafer 1 etched by using the SC-1 solution bath 2 are detected by using the dust particle inspection system.

If the sample wafer 1 has no problem in step 106, the number of detected particles of 0.12 $\mu m\phi$ or larger is, though which depends on the depth of removal from the surface of the sample wafer 1 (referred to as an "amount of removal" hereinafter), usually about several thousands. The problem means a condition in which a large number of process defects are caused in the process of mirror polishing and the like in step 102. The number of particles is increased in this case because the sizes of the pits are changed so that they can be detected by the dust particle inspection system when the sample wafer 1 is etched in the SC-1 solution bath 2.

When the sample wafer 1 has a problem, the number of detected particles of 0.12 $\mu m\phi$ or larger is usually about several tens of times greater than that in the case of no problem (about several tens of thousands). The number of particles is increased in this case because the sizes of the pits are changed to those which can be detected by the dust particle inspection system, and also because the process defects are changed into pits, when the sample wafer 1 is etched through the use of the SC-1 solution bath 2.

Figure 6:
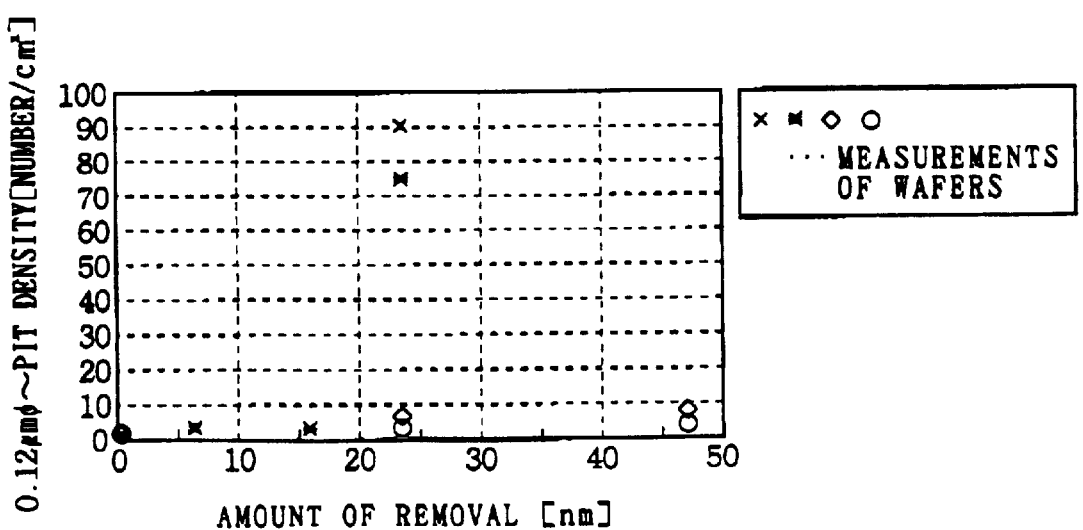
FIG. 6 is a graph showing the relation between the amount of removal and the pit density.

Next, referring to step 107, the oxide film dielectric breakdown characteristic of the semiconductor wafer is evaluated on the basis of the number of pits detected in step 106. Step 107 will now be described in detail. FIG. 6 is a graph showing examples of results obtained in steps 104–106 with sample wafers 1 in different four lots. The abscissa in FIG. 6 shows the amount of removal (unit:nm) and the ordinate shows the pit density of the detected pits (unit:number/cm2; pits of 0.12 $\mu m\phi$ or larger). As shown in FIG. 6, with the amounts of removal shallower than 20 nm, there is no significant difference among the pit densities of the sample wafers 1. However, when the amount of removal is deeper than 20 nm, a significant difference occurs in the pit density of the sample wafers 1. That is to say, the sample wafers 1 are separated into two groups depending on the magnitude of the pit density in the case where the amount of removal is deeper than 20 nm. This is because the process defects caused by the process of mirror polishing and the like in step 102 are actualized as pits which are large enough to be detected by the dust particle inspection system when the semiconductor wafer is removed to a position in the semiconductor wafer deeper than 20 nm from the surface of the semiconductor wafer. It is determined that the sample wafer 1 has no problem when the detected pit density is relatively small, and that it has a problem when the detected pit density is relatively large. For example, when the pit density of the detected pits is 10/cm2 or lower with an amount of removal larger than 20 nm, it is regarded as being nondefective, and when the pit density of the detected pits is 70/cm2 or larger, it is regarded as being defective.

Accordingly, in step 105, the sample wafer 1 must be removed to a position in the sample wafer 1 deeper than 20 nm from the surface of the sample wafer 1, with the amount of removal set deeper than 20 nm. For the conditions for obtaining amounts of removal larger than 20 nm, the etching is applied for 30 minutes or longer with the SC-1 solution set at 80° C. or higher, for example.

Figure 7:
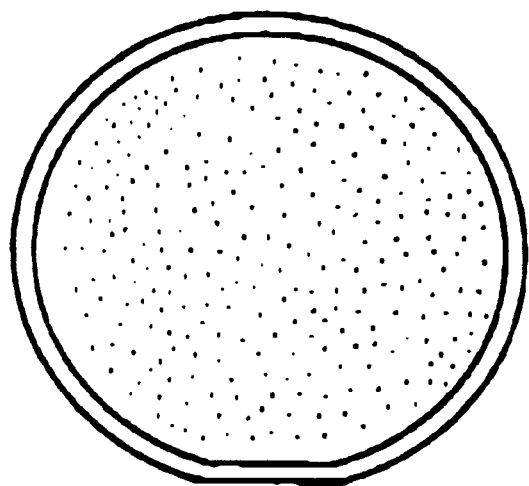
FIG. 7 to FIG. 12 are diagrams showing examples of evaluation to semiconductor wafers after mirror polished in the first preferred embodiment of the present invention.
Figure 8:
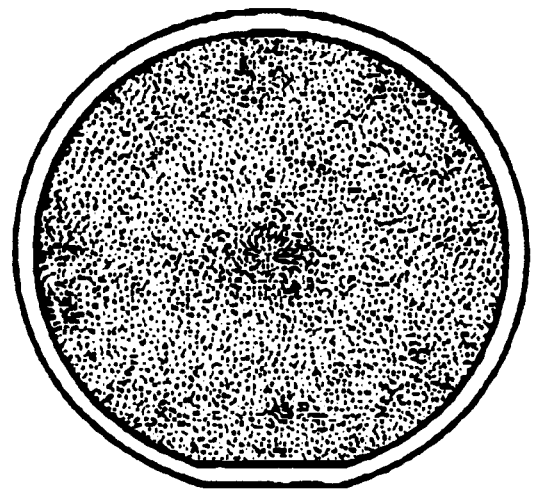
Figure 9:
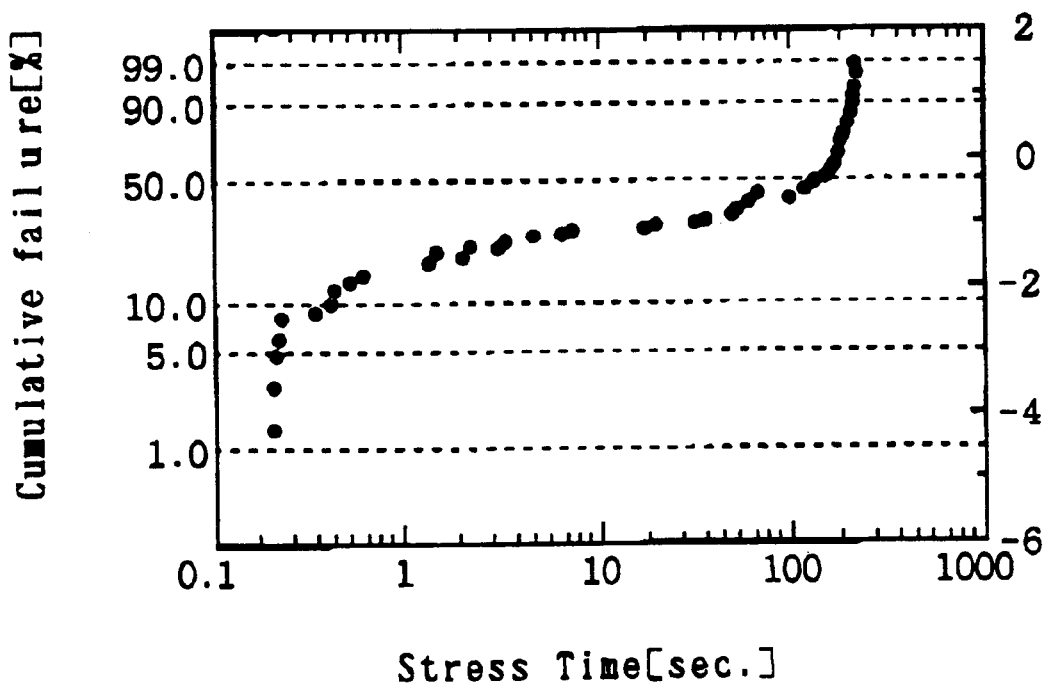
Figure 10:
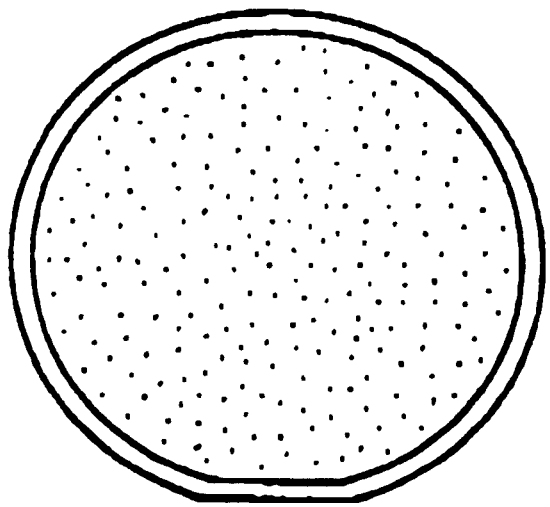
Figure 11:
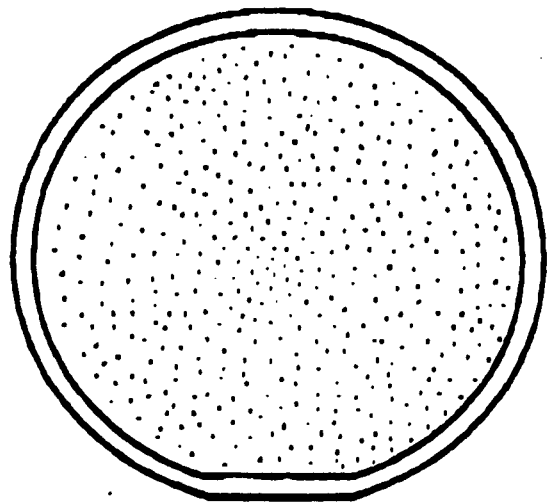
Figure 12:
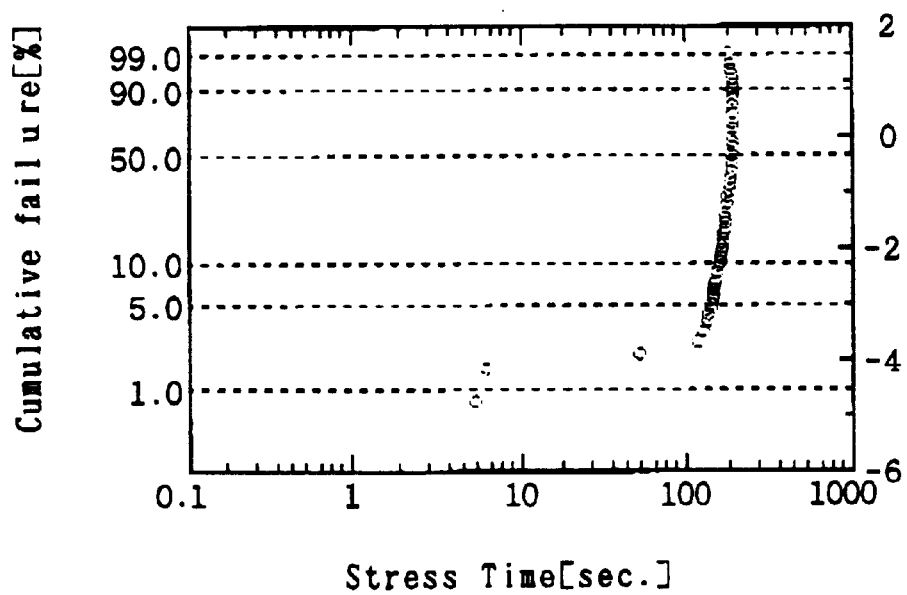

FIG. 7 to FIG. 12 show case examples obtained in steps 104 to 106 with sample wafers 1 in different lots A and B. FIG. 7 to FIG. 9 show one corresponding to the lot A (the sample wafer 1 has a size of 200 mm$\phi$). FIG. 10 to FIG. 12 show one corresponding to the lot B (the sample wafer 1 has a size of 200 mm$\phi$) separate from the lot A. FIG. 7 and FIG. 10 show particle maps (the particles have sizes of 0.12 $\mu m\phi$ or larger) of the sample wafers 1 corresponding to that shown in FIG. 2. FIG. 8 and FIG. 11 show particle maps (the particles have sizes of 0.12 $\mu m\phi$ or larger) of the sample wafers 1 corresponding to that shown in FIG. 4 (the amount of removal is 24 nm). FIG. 9 and FIG. 12 show the TDDB characteristics.

First, referring to FIG. 7 and FIG. 10, with the sample wafers 1 corresponding to that shown in FIG. 2, there is no significant difference between the distributions of the number of particles on the surfaces of the sample wafers 1 in the lot A and the lot B. Referring to FIG. 8 and FIG. 11, however, with the sample wafers 1 corresponding to that shown in FIG. 4, the distribution of the number of particles on the surface of the sample wafer 1 in the lot A significantly differs from that of the sample wafer 1 in the lot B. While the number of particles shown in FIG. 8 is largely increased to about 30000, the number of particles in FIG. 11 is about 1000. This difference is caused because the sample wafer 1 in the lot A has many process defects. Further, referring to FIG. 9 and FIG. 12, while the sample wafer 1 in the lot A causes dielectric breakdown when a certain stress is applied for about one second, the sample wafer 1 in the lot B causes no dielectric breakdown even with application of the same stress for one second. As can be seen from FIG. 7 to FIG. 12, the mirror-polished sample wafers 1 can be evaluated by utilizing etching with the SC-1 solution bath 2, without the necessity of forming a test pattern and measuring the dielectric breakdown characteristic with a dielectric breakdown characteristic measuring device in the conventional way.

Thus, a sample wafer 1 after mirror polished in another lot can be evaluated thereafter as follows. First, steps 104 to 106 are applied to the sample wafer 1. Then, the number of pits detected in step 106 is compared with previously obtained relations between the number of pits and the dielectric breakdown characteristic (herein, the relation in FIGS. 7–9 and the relation in FIGS. 10–12) to evaluate the dielectric breakdown characteristic of the sample wafer 1. If the number of pits detected in step 106 is almost equal to the number of pits in FIG. 8, for example, the dielectric breakdown characteristic of this sample wafer 1 is estimated to be similar to that shown in FIG. 9.

Since it is difficult to form reliable gate oxide film on the sample wafer 1 regarded as having a trouble in step 107, this sample wafer 1 is evaluated to be a defective product. A sample wafer 1 regarded as having no problem is evaluated to be an acceptable product.

Next, referring to step 108, when the result of evaluation in step 107 shows that the sample wafer 1 is acceptable, the lot of this sample wafer 1 is regarded as being acceptable. When the sample wafer 1 is evaluated to be a defective product, the lot of this sample wafer 1 is regarded as being defective. When a plurality of sample wafers 1 are extracted in step 103, the lot of the sample wafer 1 is taken to be defective if even one of them is evaluated to be defective.

Next, referring to steps 109 and 110, a lot evaluated to be acceptable in step 108 is managed separately from the lot judged to be defective. Next, referring to step 111, the lot of acceptable products is selected from the lots judged to be acceptable or defective on the basis of the evaluation of the sample wafers 1 and is provided into the fabrication of semiconductor devices.

Next, referring to step 112, integrated circuits are manufactured by using the semiconductor wafer 10 in the lot of acceptable products provided from step 111.

Next, referring to step 113, integrated circuits 10a having elements with predetermined Structures are formed on the semiconductor wafer 10 through step 112. These elements have gate oxide film, which are MOS transistors, IGBTs, or the like.

This way, in steps 111–113, predetermined devices are formed on the semiconductor wafers in lots regarded as acceptable products in step 108.

Figure 13:
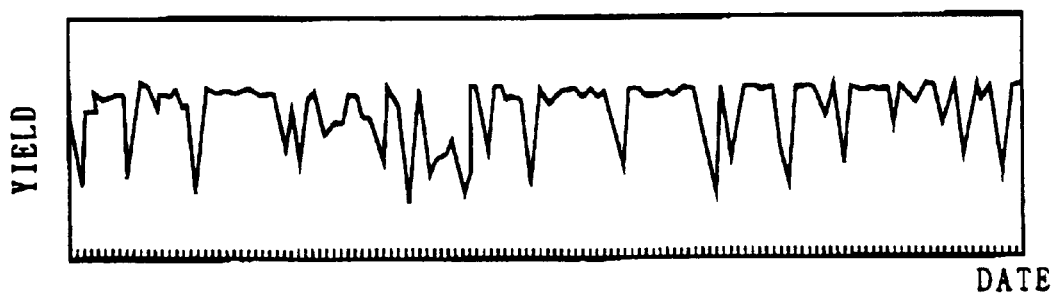
FIG. 13 is a graph showing a change of the yield of semiconductor devices manufactured without application of the semiconductor device manufacturing method of the invention.
Figure 14:
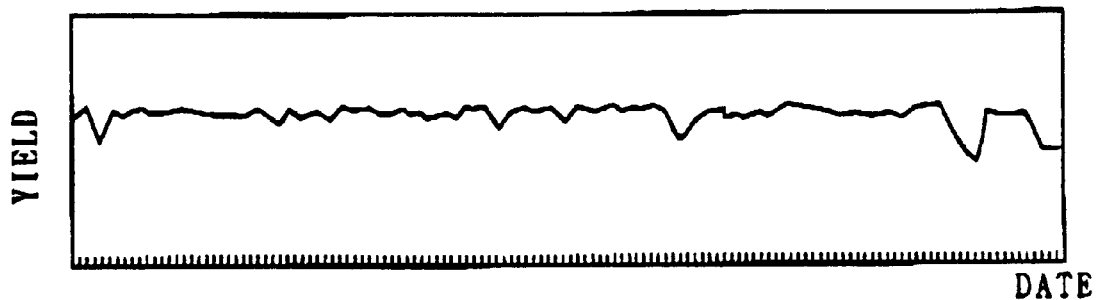
FIG. 14 is a graph showing a change of the yield of semiconductor devices manufactured by applying the semiconductor device manufacturing method of the invention.

FIG. 13 is a graph showing, with date, a change of the yield of integrated circuits 10a fabricated by providing semiconductor wafers, mirror polished in step 102, to step 112 without through steps 103–111. FIG. 14 shows, with date, a change of the yield of integrated circuits 10a fabricated by providing semiconductor wafers, mirror polished in step 102, to step 112 through steps 103–111. As can be clearly seen by comparing FIG. 13 and FIG. 14, the change of the yield of integrated circuits 10a manufactured by applying the invention shown in FIG. 14 is smaller than that of the integrated circuits 10a manufactured without applying the invention shown in FIG. 13.

The semiconductor device manufacturing method in this preferred embodiment provides the following effects:

(1) Evaluating the dielectric breakdown characteristic of the oxide film of the sample wafer 1 on the basis of the number of pits eliminates the necessity of forming the test pattern, which reduces the turn-around time, and eliminates the necessity for the use of the process device and the dielectric breakdown evaluation device.

(2) When the surface of the sample wafer 1 is removed to a position in the sample wafer 1 deeper than 20 nm from the surface of the sample wafer 1, the number of pits detected in step 106 is much larger than that in the case in which the sample wafer 1 is removed to a position shallower than 20 nm from the surface. That is to say, removing the surface of the sample wafer 1 to a position deeper than 20 nm from the surface of the sample wafer 1 enables more accurate detection of the total number of process defects caused by the process of mirror polishing and the like.

(3) A semiconductor wafer is extracted from a plurality of semiconductor wafers in a lot as a sample wafer 1 and the extracted sample wafer 1 is evaluated. Then the remaining semiconductor wafers in the lot are managed as products evaluated equally to the extracted sample wafer, which eliminates the necessity of evaluating each semiconductor wafer and enables simple management.

(4) Selecting semiconductor wafers on the basis of the evaluation of the sample wafer 1 and forming semiconductor devices on the selected semiconductor wafers provides semiconductor devices with improved quality, and improves the yield of the semiconductor devices and suppresses the change in the yield.

(5) Removing the surface of the sample wafer 1 by using the SC-1 solution bath 2 can change process defects caused by process of mirror polishing or the like into pits, and can also change defects under the semiconductor wafer surface into pits large enough to be detected by a dust particle inspection system.

Second Preferred Embodiment

Next, a semiconductor device manufacturing method in a second preferred embodiment of the present invention will be described referring to FIG. 1 and FIG. 15 to FIG. 18. Although this preferred embodiment is similar to the semiconductor device manufacturing method shown in FIG. 1, it differs in steps 104 to 107. Steps 104 to 107 in this preferred embodiment are now described.

Figure 15:
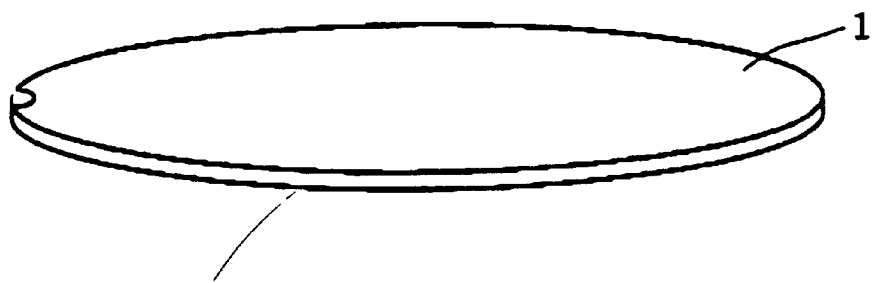
FIG. 15 is a drawing schematically showing a particle number detecting step in FIG. 1 in a second preferred embodiment of the present invention.

Referring to step 104, the number of particles on the surface of the sample wafer 1 shown in FIG. 15 is detected with a dust particle inspection system. The sample wafer 1 shown in FIG. 15 is an example of a sample wafer extracted in step 103. The sample wafer 1 shown in FIG. 15 has a size of 200 mmφ and it is mirror polished. For the dust particle inspection system, Surfscan6200 produced by Tencor is used, for example. This device detects particles having sizes of about 0.10 to 0.14 μmφ or larger. It is now assumed that process defects are caused by the process of mirror polishing or the like on the plurality of semiconductor wafers in the lot prepared in step 102.

When the sample wafer 1 is manufactured on a processing line with cleanliness sufficiently controlled, the number of the particles of 0.12 $\mu$m$\phi$ or larger is usually 0–100. In this case, the particles mainly include the pits 1*ba*, since the dust particles 1*b* attached on the surface of the sample wafer 1 (refer to FIG. 5) are cleaned away.

If the number of particles detected in stop 104 is larger than a predetermined number, it is possible, at this point of time, to determine that the plurality of semiconductor wafers in the lot of this sample wafer 1 are all defective products.

Figure 16:
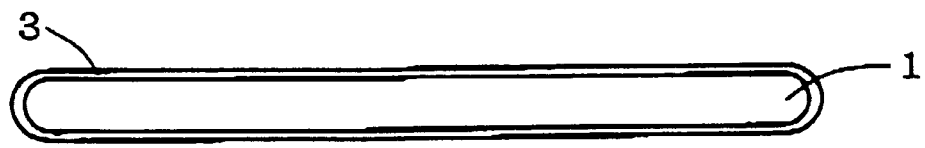
FIG. 16 is a drawing schematically showing a process strain changing step in FIG. 1 in a second preferred embodiment of the present invention.
Figure 17:
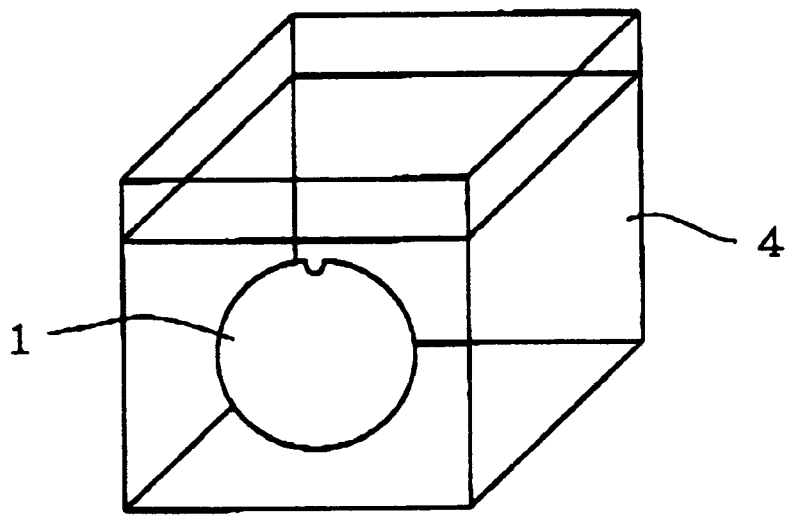
FIG. 17 is a drawing schematically showing a process strain changing step in FIG. 1 in a second preferred embodiment of the present invention.

Next, referring to step 105, the sample wafer 1 is oxidized by heating (thermally oxidized), as shown in FIG. 16, to form a thermal oxide film 3 on the surface of the sample wafer 1. Particularly, the thermal oxide film 3 has a larger thickness on process defects than in the area with no process defects. Next, as shown in FIG. 17, the sample wafer 1 with the thermal oxide film 3 formed thereon is immersed into a hydrofluoric acid (HF) solution bath 4 filled with hydrofluoric acid. This hydrofluoric acid can remove only the thermal oxide film 3 without dissolving the semiconductor wafer. Another solution which can remove only the thermal oxide film 3 without dissolving the semiconductor wafer may be substituted for hydrofluoric acid in the hydrofluoric acid solution bath 4. Immersing the sample wafer 1 into the hydrofluoric acid solution bath 4 removes the thermal oxide film 3, or removes the surface of the sample wafer 1. Since the thickness of the thermal oxide film 3 formed on process defects is larger, the process defects are changed into pits. Thus the defects under the surface of the semiconductor wafer, or the pits originated from the process defects and the defects already existing in step 102 are changed by the etching into pits large enough to be detected by the dust particle inspection system.

In step 105, the dust particles 1*b* (refer to FIG. 5) attached on the surface of the sample wafer 1 in FIG. 15 are removed simultaneously with the removal of the thermal oxide film 3. Thus, in step 105, heating the sample wafer 1 to form a thermal oxide film on the surface and then removing the oxide film by using hydrofluoric acid changes the process defects caused in the process such as mirror polishing into pits, and also changes the defects under the surface of the semiconductor wafer into pits large enough to be detected by the dust particle inspection system.

Figure 18:
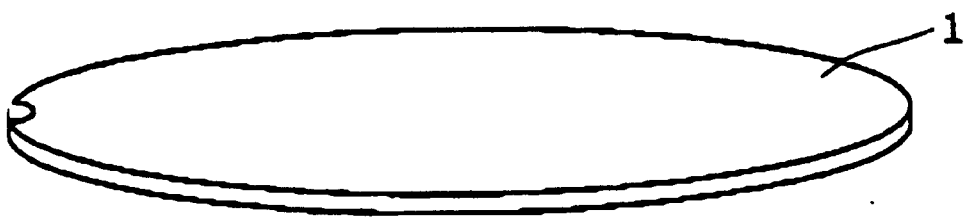
FIG. 18 is a drawing schematically showing a pit number detecting step in FIG. 1 in a second preferred embodiment of the present invention.

Next, after step 105, referring to step 106, the sample wafer 1 is taken out from the hydrofluoric acid solution bath 4. The sample wafer 1 shown in FIG. 18 shows the sample wafer taken out from the hydrofluoric acid solution bath 4. Since the dust particles have been removed in step 105 as stated above, the particles on the surface of the sample wafer 1 taken out from the hydrofluoric acid solution bath 4 mainly include pits. Then the number of the pits on the surface of the sample wafer 1 etched by using the hydrofluoric acid solution bath 4 is detected by using the dust particle inspection system.

If the sample wafer 1 has no problem in step 106, the number of detected particles of 0.14 $\mu$m$\phi$ or larger, though which depends on the amount of removal, is usually about several hundreds. The problem means, as described in the first preferred embodiment, a condition in which a large number of process defects are caused in the process of mirror polishing or the like in step 102 of FIG. 1. The number of particles is increased in this case because the sizes of the pits are changed so that they can be detected by the dust particle inspection system when the thermal oxide film 3 is removed.

When the sample wafer 1 has a problem, the number of detected particles of 0.12 $\mu$m$\phi$ or larger is usually about several tens of times greater than that in the case of no problem (about several thousands). The number of particles is increased in this case because the sizes of the pits were changed to those which can be detected by the dust particle inspection system when the thermal oxide film 3 was removed, and also because the process defects were changed into pits.

Next, referring to step 107, the dielectric breakdown characteristic of the oxide film of the semiconductor wafer is evaluated on the basis of the number of pits detected in step 106. Step 107 will now be described in detail. Also in this preferred embodiment, as has been described in the first preferred embodiment, with amounts of removal shallower than 20 nm, there is no significant difference among the pit densities of the sample wafers 1. However, when the amount of removal is deeper than 20 nm, a significant difference occurs in the pit density of the sample wafers 1. That is to say, the sample wafers 1 are separated into two groups depending on the magnitude of the pit density in the case where the amount of removal is deeper than 20 nm. It is determined that the sample wafer 1 has no problem when the detected pit density is relatively small, and that it has a problem when the detected pit density is relatively large.

Accordingly, in step 105, the sample wafer 1 must be removed to a position in the sample wafer 1 deeper than 20 nm from the surface of the sample wafer 1, with the amount of removal set to 20 nm or larger.

Figure 19:
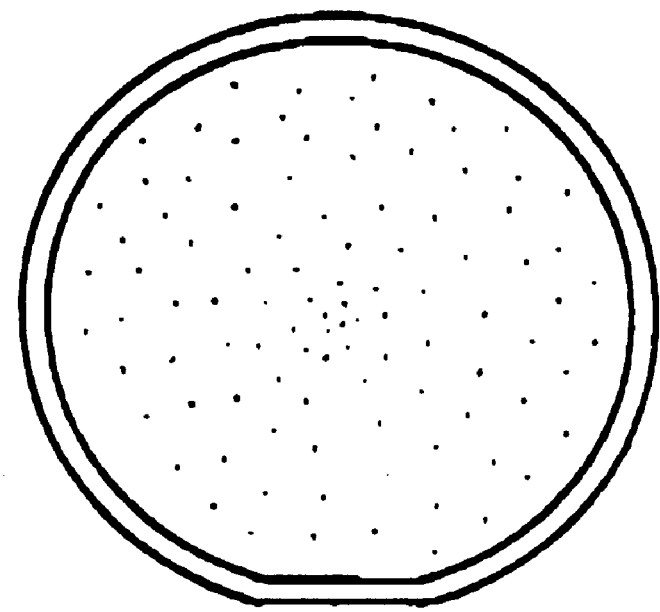
FIG. 19 to FIG. 22 are diagrams showing examples of evaluation to semiconductor wafers after mirror polished in the second preferred embodiment of the present invention.
Figure 20:
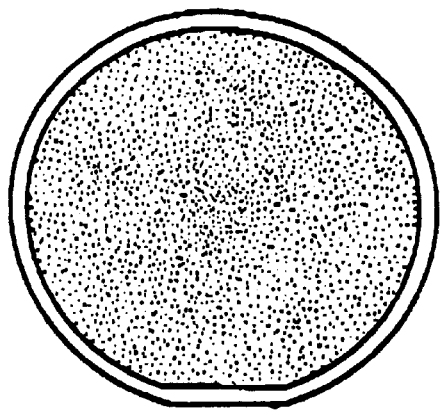
Figure 21:
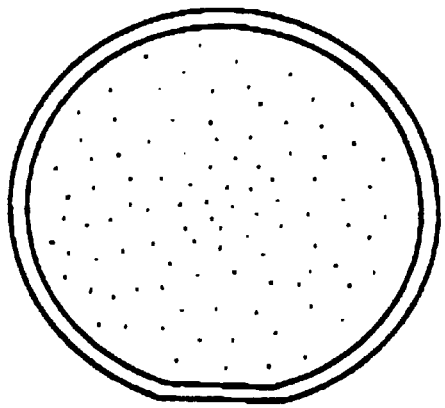
Figure 22:
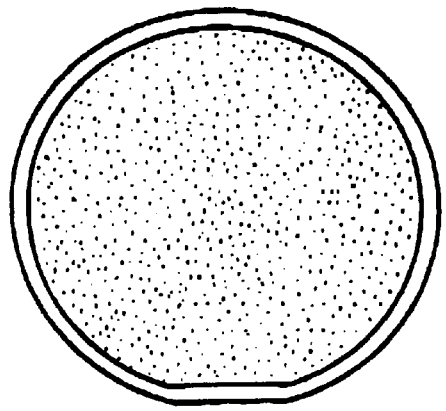

FIG. 19 to FIG. 22 show case examples obtained in steps 104 to 106 with sample wafers 1 in different lots A and B. FIG. 19 and FIG. 20 show one corresponding to the lot A (the sample wafer 1 has a size of 200 mm$\phi$). FIG. 21 and FIG. 22 show one corresponding to the lot B (the sample wafer 1 has a size of 200 mm$\phi$) separate from the lot A. FIG. 19 and FIG. 21 show particle maps (the particles have sizes of 0.14 $\mu$m$\phi$ or larger) of the sample wafers 1 corresponding to that shown in FIG. 15. FIG. 20 and FIG. 22 show particle maps (the particles have sizes of 0.14 $\mu$m$\phi$ or larger) of the sample wafers 1 corresponding to that shown in FIG. 18 (the thickness of the thermal oxide film 3 is 400 nm, that is, the amount of removal is deeper than 20 nm).

First, referring to FIG. 19 and FIG. 21, with the sample wafers 1 corresponding to that shown in FIG. 15, there is no significant difference between the distributions of the number of particles on the surfaces of the sample wafers 1 in the lot A and the lot B. Referring to FIG. 20 and FIG. 22, however, with the sample wafers 1 corresponding to that shown in FIG. 18, the distribution of the number of particles on the surface of the sample wafer 1 in the lot A significantly differs from that of the sample wafer 1 in the lot B. While the number of particles shown in FIG. 20 is largely increased to about 15000, the number of particles in FIG. 22 is about 1500. This difference is caused because the sample wafer 1 in the lot A has many process defects. Further, as described in the first preferred embodiment, referring to FIG. 9 and FIG. 12, while the sample wafer in the lot A causes dielectric breakdown when a certain stress is applied for about one second, the sample wafer in the lot B causes no dielectric breakdown even with application of the same stress for one second. As can be seen from FIGS. 19–22 and FIG. 9 and FIG. 12, the finally mirror-polished sample wafers 1 can be evaluated by utilizing formation and removal of the thermal oxide film 3, without forming a test pattern and measuring the TDDB characteristic with a dielectric breakdown characteristic measuring device in the conventional way.

Thus, a finally mirror-polished sample wafer 1 in another lot can be evaluated thereafter as follows. First, steps 104 to 106 are applied to the sample wafer 1. Then, the number of pits detected in step 106 is compared with previously obtained relations between the number of pits and the dielectric breakdown characteristic (herein, the relation in FIGS. 19, 20, 9, and the relation in FIGS. 21, 22, 12) to evaluate the dielectric breakdown characteristic of the sample wafer 1. If the number of pits detected in step 106 is almost equal to the number of pits in FIG. 20, for example, the dielectric breakdown characteristic of this sample wafer 1 is estimated to be similar to that shown in FIG. 9.

Since it is difficult to form reliable gate oxide film on the sample wafer 1 determined as having a trouble in step 107, this sample wafer 1 is evaluated to be a defective product. A sample wafer 1 determined as having no problem is evaluated to be an acceptable product.

The semiconductor device manufacturing method in this preferred embodiment provides the following effect in addition to the effects (1) to (4) described in the first preferred embodiment.

(6) Heating the sample wafer 1 to form a thermal oxide film 3 on the surface of the sample wafer 1 and then removing the thermal oxide film 3 by using hydrofluoric acid can change the process defects caused in processes such as mirror polishing into pits, and can also change the pits under the semiconductor wafer surface into pits large enough to be detectable by the dust particle inspection system.

While the invention has been described in detail, the foregoing description is in all aspects illustrative and not restrictive. It is understood that numerous other modifications and variations can be devised without departing from the scope of the invention.

We claim:

1. A semiconductor wafer evaluation method comprising the steps of:

(a) preparing a mirror-polished semiconductor wafer;

(b) changing a process defect caused by grinding and polishing including said mirror polishing into a pit and also changing a defect under the surface of said semiconductor wafer into a pit having a detectable size;

(c) detecting the number of pits on said semiconductor wafer surface after said stop (b); and (d) evaluating a probability of an oxide film dielectric breakdown relative said semiconductor wafer on the basis of the number of pits detected in said step (c).

2. The semiconductor wafer evaluation method according to claim 1, wherein said step (b) further comprises the step of removing said semiconductor wafer to a position deeper than 20 nm in said semiconductor wafer from the surface of said semiconductor wafer.

3. The semiconductor wafer evaluation method according to claim 2, wherein said step (b) further comprises the step of removing the surface of said semiconductor wafer by using a mixed solution of $NH_4OH$, $H_2O_2$, and $H_2O$.

4. The semiconductor wafer evaluation method according to claim 2, wherein said step (b) further comprises the step of heating said semiconductor wafer to form an oxide film on the surface of said semiconductor wafer and then removing said oxide film by using a solution which can remove only said oxide film without dissolving said semiconductor wafer.

5. The semiconductor wafer evaluation method according to claim 1, wherein said step (a) further comprises the steps of (a-1) preparing a plurality of semiconductor wafers in a certain lot, and (a-2) extracting a certain number of semiconductor wafer(s) as sample wafer(s) from said plurality of semiconductor wafers in said lot, wherein said semiconductor wafer evaluation method further comprises the step of (e) judging said lot to be acceptable when the evaluation in said step (d) shows that said sample wafer is acceptable.

6. A semiconductor device manufacturing method comprising the steps of:

(a-1) preparing a plurality of mirror-polished semiconductor wafers in a certain lot;

(a-2) extracting predetermined number of semiconductor wafer(s) as sample wafer(s) from said plurality of semiconductor wafers in said lot;

(b) changing a process defect caused by grinding and polishing including said mirror polishing into a pit and also changing a defect under the surface of said sample wafer(s) into a pit having a detectable size;

(c) detecting the number of pits on said sample wafer(s) surface after said step (b);

(d) evaluating a probability of an oxide film dielectric breakdown relative to of said sample wafer(s) on the basis of the number of pits detected in said step (c); and (e) judging said lot to be acceptable when the evaluation in said step (d) shows that said sample wafer is acceptable, wherein predetermined semiconductor devices are formed on said semiconductor wafers in the lot which is judged to be acceptable in said step (e).

* * * * *

UNITED STATES PATENT AND TRADEMARK OFFICE
CERTIFICATE OF CORRECTION

PATENT NO. : 5,946,543
DATED : August 31, 1999
INVENTOR(S) : Yasuhiro KIMURA, et al.

It is certified that error appears in the above-identified patent and that said Letters Patent is hereby corrected as shown below:

On the title page, item [73], the first assignee's name should be:

--Mitsubishi Denki Kabushiki Kaisha--

Signed and Sealed this

Sixth Day of June, 2000

Attest:

Q. TODD DICKINSON

*Attesting Officer*      *Director of Patents and Trademarks*